(12) United States Patent
Ronsen et al.

(10) Patent No.: US 6,638,948 B1
(45) Date of Patent: *Oct. 28, 2003

(54) AMORPHOUS PAROXETINE COMPOSITION

(75) Inventors: Bruce Ronsen, River Forest, IL (US); Ragab El-Rashidy, Deerfield, IL (US)

(73) Assignee: Pentech Pharmaceuticals, Inc., Rolling Meadows, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/940,058

(22) Filed: Sep. 30, 1997

Related U.S. Application Data

(63) Continuation-in-part of application No. 08/708,802, filed on Sep. 9, 1996, now Pat. No. 5,672,612.

(51) Int. Cl.⁷ .................. A61K 31/445; C07D 409/12
(52) U.S. Cl. ........................... 514/321; 546/197
(58) Field of Search ............... 514/338, 321; 546/197

(56) References Cited

U.S. PATENT DOCUMENTS

| | | | |
|---|---|---|---|
| 4,007,196 A | 2/1977 | Christensen et al. ... | 260/293.58 |
| 4,721,723 A | 1/1988 | Barnes et al. ........... | 514/321 |
| 4,902,801 A | 2/1990 | Faruk et al. ........... | 546/220 |
| 5,151,448 A | 9/1992 | Crenshaw et al. ....... | 514/651 |
| 5,258,517 A | 11/1993 | Zepp et al. ............ | 546/240 |
| 5,276,042 A | 1/1994 | Crenshaw et al. ....... | 514/321 |
| 5,399,584 A * | 3/1995 | Ares et al. ............. | 514/432 |
| 5,811,436 A * | 9/1998 | Leonard et al. ......... | 514/321 |
| 5,955,475 A * | 9/1999 | Krape et al. ........... | 514/321 |
| 2001/0021776 A1 * | 9/2001 | Wang et al. ........... | 546/197 |

FOREIGN PATENT DOCUMENTS

| | | | |
|---|---|---|---|
| GB | 2297550 * | 7/1996 | |
| WO | EP-A-0 212 641 | 3/1987 | ............. A61K/9/22 |
| WO | WO-A-95 15155 | 6/1995 | ............. A61K/9/16 |
| WO | WO-A-95 16448 | 6/1995 | ......... A61K/31/445 |
| WO | WO-A-95 20964 | 8/1995 | ......... A61K/31/445 |
| WO | WO-A-96 24595 | 8/1996 | ......... C07D/405/12 |
| WO | WO 96/41617 * | 12/1996 | |
| WO | WO-A-97 03670 | 2/1997 | ......... A61K/31/445 |
| WO | WO-A-97 24323 | 7/1997 | ......... C07D/211/22 |

OTHER PUBLICATIONS

Evans et al. "An introduction to Crystal Chemistry" Cambridge press, p. 394–396 (1964).*

Traue et al. "Spray-embedding of low solubility . . . " CA 113:46223f, 1990.*

Uekama et al. "Inhbitory effecto of 2–hydroxypropyl cyclodextrin . . . " CA 116:158767d, 1992.*

Byron et al. "Drug carrier selection . . . " CA 125:95823g, Aug. 1996.*

Borodkin et al. "interaction of amine drugs with a polycarboxylic acid ion exchanger resin" J. Pharm. Sci. v59(4) p. 481–86, 1970.*

Lieberman et al. "pharmaceutical dosage forms" marcel Dekker Inc. p.462–463, 1990.*

Kai et al. "Oral absorption improvement of poorly soluble drug using solid dispersion technique" chem. Pharm. bull. v.44(3) 568–571, Mar. 1996.*

Lin et al. "Studies on drug interaction . . . " CA 112:83982b, 1990.*

Lachman et al. "The theory and practice of industrial pharmacy" Lea and Febiger, p. 326–342 (1976).*

Hilderbrand, G.E., et al. Preparation and Its Formation of Mixed Crystals with Ketoprofen, *J. Pharmaceutical Sciences* 86:854–857.

Buxton, P.C., et al. Solid–state forms of paroxetine hyrochloride, *Int. J. Pharmaceutics* 42:135–143.

Matsuda, Y, et al. Amorphism and Physicohemical Stability of Spray–dried Frusemide, *J. Pharm. Pharmacol* 44:627–633.

Schmitt, C.W., et al. *J. Pharmaceutical Sciences* 85: 1215–219.

Wu, L.S., et al. Investigation of Moricizine Hydrochloride Polymorphs *J. Pharmaceutical Sciences* 83: 1404–1406.

Yoshioka, M., et al. *J. Pharmaceutical Sciences* 84:983–986.

Lund J., et al. Paroxetine: Pharmacokinetics, Tolerance and Depletion . . . *Acta pharmacol. et toxicol.* 44:289–295.

* cited by examiner

*Primary Examiner*—Ceila Chang
(74) *Attorney, Agent, or Firm*—Olson & Hierl, Ltd.

(57) ABSTRACT

A free-flowing, amorphous paroxetine hydrochloride composition suitable as a therapeutic agent for premature ejaculation can be prepared by dissolving paroxetine free base in a hydrochloric acid-ethanol solution followed by drying. The present compositions comprise amorphous paroxetine hydrochloride and at least one hydroxyl-bearing compound. In one preferred embodiment, the hydroxyl-bearing compound is ethanol and the amount of ethanol present in the amorphous product is in the range of 1 to 4 weight percent based on paroxetine hydrochloride. The amorphous product is stable and substantially non-hygroscopic.

15 Claims, 14 Drawing Sheets

AMORPHOUS PAROXETINE COMPOSITION

REFERENCE TO RELATED APPLICATION

This is a Continuation-In-Part Application of U.S. Ser. No. 08/708,802, filed Sep. 9, 1996, which issued as U.S. Pat. No. 5,672,612.

FIELD OF THE INVENTION

This invention relates to an amorphous paroxetine composition suitable as a therapeutic agent for sexual dysfunction and to a process for preparing such composition.

BACKGROUND OF THE INVENTION

The selective serotonin reuptake inhibitor (SSRI) antidepressants have recently emerged as effective new treatments for patients with premature ejaculation. In general, antidepressants influence more than one neurotransmitter system and have affinity for multiple receptors. This heterogeneity of action produces mixed effects, including those on the sexual response cycle. Sexual dysfunction associated with antidepressants, including delayed and completely abolished ejaculation, has been a subject of numerous case reports, studies, and review articles [for example, *J. Clin. Psychiatry* 54, 209–212, (1993); *J. Clin. Psychopharmacol.* 3, 76–79, (1983); *J. Clin. Psychiatry Mon.* 10, 4–10, (1992); *Depression* 2, 233–240, (1994/1995)]. Because of the lack of abuse potential, relatively benign side effect profile, and fairly consistent reports of delayed ejaculation, SSRI antidepressants seem to be a safe treatment option for patients with premature ejaculation, especially in cases of failed psychological treatment.

The use of the SSRI antidepressant fluoxetine hydrochloride (PROZAC®) in this regard has been described in U.S. Pat. No. 5,151,448 to Crenshaw et al. A similar treatment, at a relatively lower dosage of active ingredient, has been described in U.S. Pat. No. 5,276,042 to Crenshaw et al. for the SSRI antidepressant paroxetine hydrochloride (PAXIL®). Other anti-anxiety drugs such as chlordiazepoxide (LIBRIUM®) and diazepam (VALIUM®) are not suitable for the treatment of premature ejaculation.

The preparation of a class of SSRI antidepressants has been disclosed in U.S. Pat. No. 4,007,196 to Christensen et al. In Example 2 of this patent, the preparation of (–)-trans4R-(4'-fluorophenyl)-3S-[(3'4'-methylenedioxyphenoxy)methyl]-piperidine (generic name paroxetine) is described (formula A),

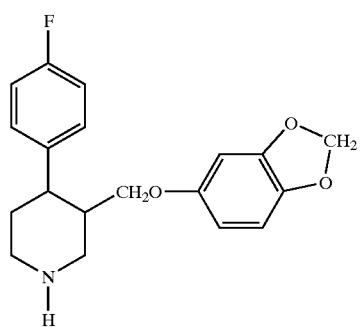

(A)

wherein paroxetine is obtained as a free base then converted to its maleic acid salt. The use of the acetate salt of paroxetine has been described [*Psychopharmacology* 57, 151–153 (1978); *Psychopharmacology* 68, 229–233 (1980); *European Journal of Pharmacology* 47, 351–358 (1978)]. There also has been limited use of the hydrochloride salt in aqueous solution [*Acta. Pharmacol. et Toxicol.* 44, 289–295 (1979)]. More recently, U.S. Pat. No. 4,721,723 to Barnes et al. has disclosed the preparation of a crystalline paroxetine hydrochloride hemihydrate. However, this particular process requires post-synthetic treatment of the product in order to obtain the crystalline form, which adds to the difficulty and overall cost of production. Amorphous paroxetine hydrochloride has been reported by Barnes et al. to be undesirably hygroscopic.

The present invention provides an economical manufacturing process for the preparation of a substantially non-hygroscopic, free-flowing, amorphous paroxetine hydrochloride-ethanol composition suitable as a therapeutic agent for the treatment of premature ejaculation.

SUMMARY OF THE INVENTION

Compositions of amorphous paroxetine hydrochloride and a hydroxyl-bearing compound, as well as methods for production of such compositions are disclosed. The present inventive method generates amorphous, substantially non-hygroscopic paroxetine hydrochloride from a reaction of paroxetine base with a hydrochloric acid/ethanol solution followed by drying of the product. This invention overcomes inherent problems associated with crystallization methods of the prior art, including the recovery of product. The composition embodying the present invention is eminently well suited for the preparation of tablet dosage forms containing paroxetine.

The paroxetine base can be prepared according to the procedure set forth in U.S. Pat. No. 4,007,196 to Christensen et al. Paroxetine hydrochloride solute is obtained by combining an appropriate amount of hydrochloric acid in absolute ethanol with the free base. The amorphous composition is produced upon drying of the product. In a preferred embodiment, the amount of ethanol present in the product is not more than about 10 percent by weight based on the paroxetine hydrochloride. Under this condition, the amorphous composition is a substantially non-hygroscopic solid, thus providing a manufacturing advantage. In a more preferred embodiment, the amount of ethanol present in the composition is in the range of about 1 to about 4 weight percent, based on paroxetine hydrochloride. This amorphous composition is stable and is amenable to incorporation into both tablet and suppository dosage forms.

At least one compound having at least hydroxyl moiety, i.e., an hydroxyl-bearing compound, can be used in addition to, or instead of, ethanol or other monohydric alcohol in making the amorphous paroxetine composition of the present invention. Addition of one or more hydroxyl-bearing compounds to the composition is useful in improving the stability of the amorphous paroxetine composition as measured by color and by paroxetine content. Suitable hydroxyl-bearing compounds are carboxylic acids, hydroxycarboxylic acids, sugar acids, polyhydric alcohols and cyclodextrins. A preferred hydroxycarboxylic acid is citric acid. A preferred polyhydric alcohol is D-mannitol. A preferred cyclodextrin is hydroxypropyl-beta-cyclodextrin.

DETAILED DESCRIPTION OF PREFERRED EMBODIMENTS

Figure 1:
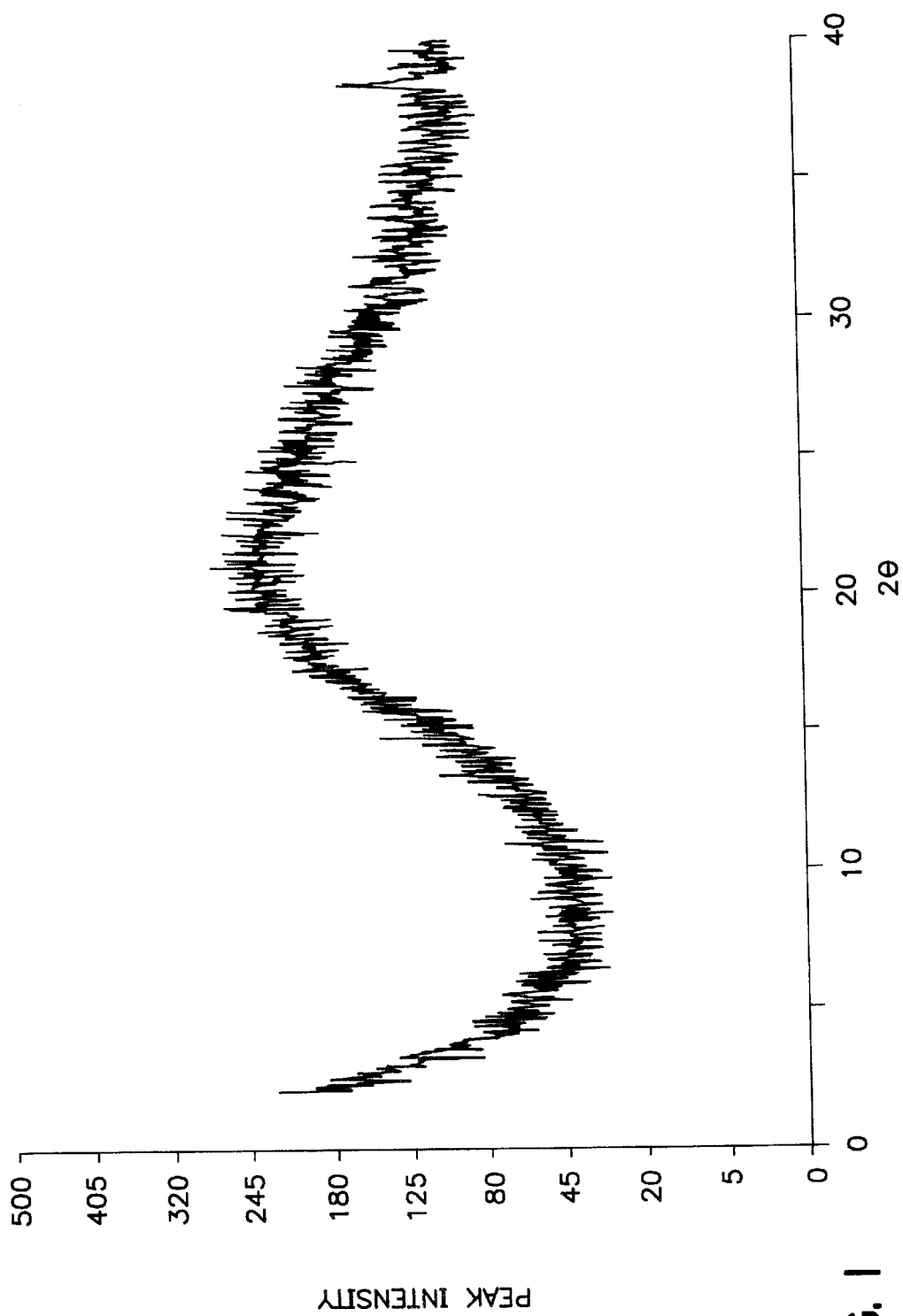
FIG. 1 is the diffraction pattern of the amorphous paroxetine composition, lot # W951027. The horizontal axis represents 2θ and the vertical axis corresponds to peak intensity.

A free-flowing, substantially non-hygroscopic solid form of paroxetine hydrochloride-ethanol is obtained by combining paroxetine base with a hydrochloric acid/ethanol solution and drying of the product. The drying step can be effected by spray-drying, vacuum drying and the like.

The paroxetine base can be obtained according to the procedure of U.S. Pat. No. 4,007,196 to Christensen et al. Absolute ethanol is added in an amount sufficient to dissolve the paroxetine base, the molar ratio of paroxetine base to absolute ethanol preferably being in the range of about 10% v/v to about 15% w/v. A solution of hydrochloric acid in absolute ethanol preferably in the range of about 10% v/v to about 30% v/v, usually about 22% v/v, is added to the paroxetine base solution and stirred at ambient temperature and pressure for a time period sufficient to produce paroxetine hydrochloride salt. The preferred molar ratio of paroxetine base to hydrochloric acid is in the range of about 1:1 to about 1:10. The reaction temperature is preferably in the range of about 15 degrees Celsius to about 40 degrees Celsius along with a preferred reaction time in the range of about 10 minutes to about 40 minutes. The resulting solution is then dried by rotary evaporation or spray drying to obtain the desired amorphous paroxetine hydrochloride-ethanol composition. The drying time preferably ranges from about 8 hours to about 72 hours. The amount of ethanol present in the final product relative to paroxetine hydrochloride is not more than about 10 weight percent, more preferably in the range of about 1 to about 4 weight percent.

At least one compound having at least hydroxyl moiety, i.e., an hydroxyl-bearing compound, can be used in addition to, or instead of, ethanol or other monohydric alcohol in making the amorphous paroxetine composition of the present invention. Addition of one or more hydroxyl-bearing compounds to the composition is useful in improving the stability of the amorphous paroxetine composition as measured by color and by paroxetine content. Suitable hydroxyl-bearing compounds are a carboxylic acid, a hydroxycarboxylic acid, a sugar acid, a polyhydric alcohol, a cyclodextrin and mixtures thereof.

Suitable carboxylic acids include acetic acid, maleic acid, succinic acid, propionic acid, butyric acid, valeric acid, caproic acid, enanthic acid, caprylic acid, and the like. Suitable hydroxycarboxylic acids include citric acid, malic acid, tartaric acid, lactic acid and the like. The preferred hydroxycarboxylic acid is citric acid. Citric acid is preferably present in an amount from about 3 to about 25 weight percent based on the weight of the amorphous paroxetine hydrochloride.

Sugar acids include aldonic acids, aldaric acids and uronic acids. Suitable aldonic acids are D-glyceric acid, D-gluconic acid, L-gulonic acid, L-ascorbic acid and the like. L-ascorbic acid is a preferred aldonic acid. An illustrative aldaric acid is D-glucaric acid. Suitable uronic acids include alpha-D-galacturonic acid, beta-D-glucuronic acid, D-mannuronic acid, L-iduronic acid and the like.

Polyhydric alcohols include propylene glycol, polyethylene glycol, L-sorbitol, D-mannitol, glycerol, inositol and the like. A preferred polyhydric alcohol is D-mannitol.

Cyclodextrins includes alpha-cyclodextrin, beta-cyclodextrin, gamma-cyclodextrin as well as substituted cyclodextrins such as 2-methylcyclodextrin and hydroxypropyl-beta-cyclodextrins. Hydroxypropyl-beta-cyclodextrins are commercially available compounds that are derived from beta-cyclodextrins by condensation with propylene oxide to provide the corresponding hydroxypropyl derivatives. For the purpose of the present invention, a degree of substitution corresponding to 0.5 to 0.7 hydroxypropyl substituents per glucose residue of the beta-cyclodextrin is preferable. A degree of substitution corresponding to about 0.6 hydroxypropyl substituents per glucose residue of the beta-cyclodextrin is preferred.

Excipients known to one skilled in the art can be added to the amorphous paroxetine composition of the present invention to facilitate the formation of dosage forms such as tablets or capsules. Such excipients include polyvinyl pyrrolidone (PVP), dicalcium phosphate dehydrate, lactose monohydrate, microcrystalline cellulose (such as Avicel PH102), sodium starch glycolate and fumed silica. Polyvinyl pyrrolidone is preferably present in the amount of from about 20 to about 340 weight percent based on the weight of the amorphous paroxetine hydrochloride.

EXAMPLE 1

Figure 3A:
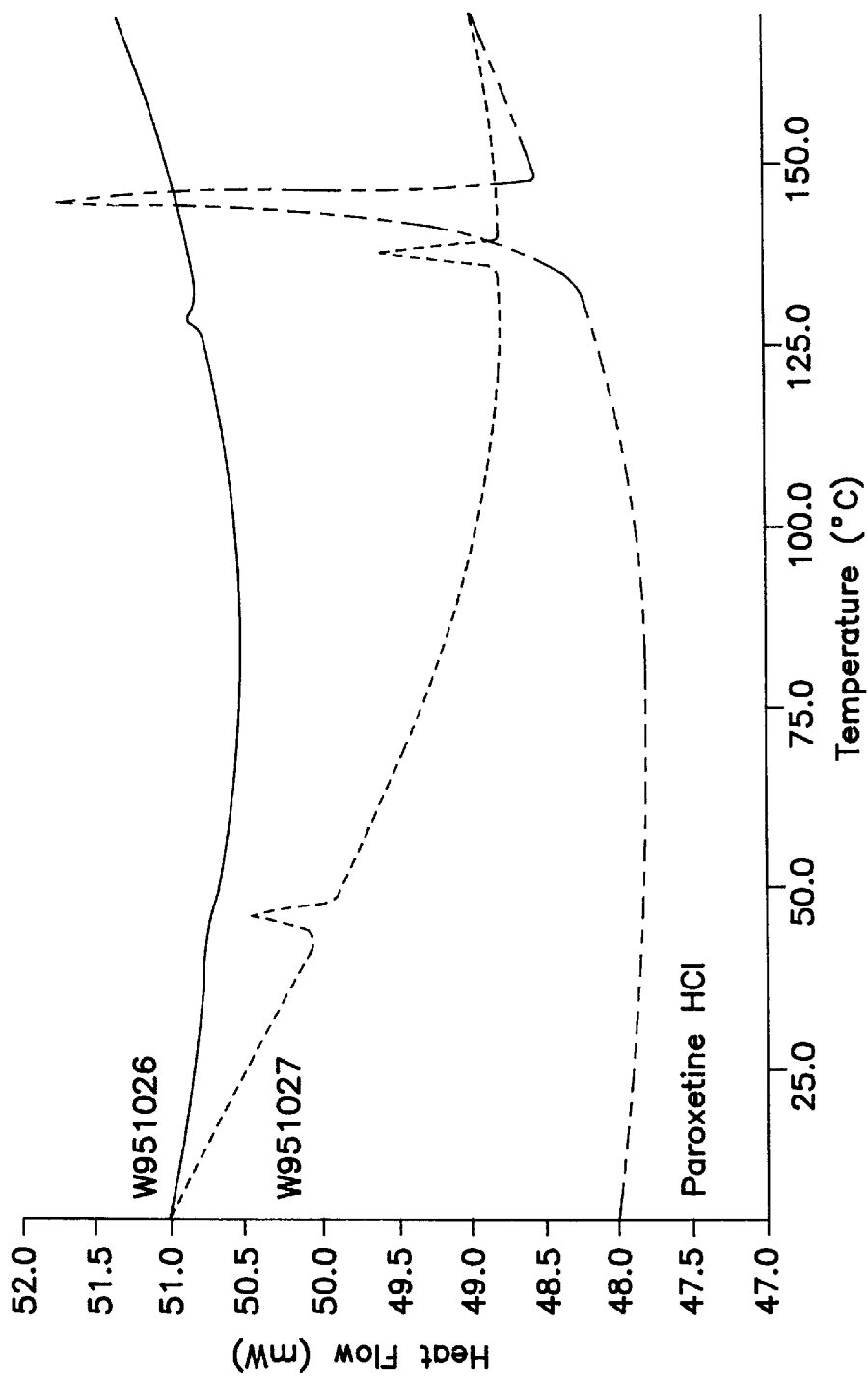
FIG. 3A illustrates the results of differential scanning calorimetry done at a heating rate of 5 degrees Celsius/minute on the reference sample paroxetine hydrochloride and two amorphous samples, lot #'s W951027 and W951026. The horizontal axis represents temperature (degrees Celsius) and the vertical axis corresponds to the heat flow (mW).
Figure 3B:
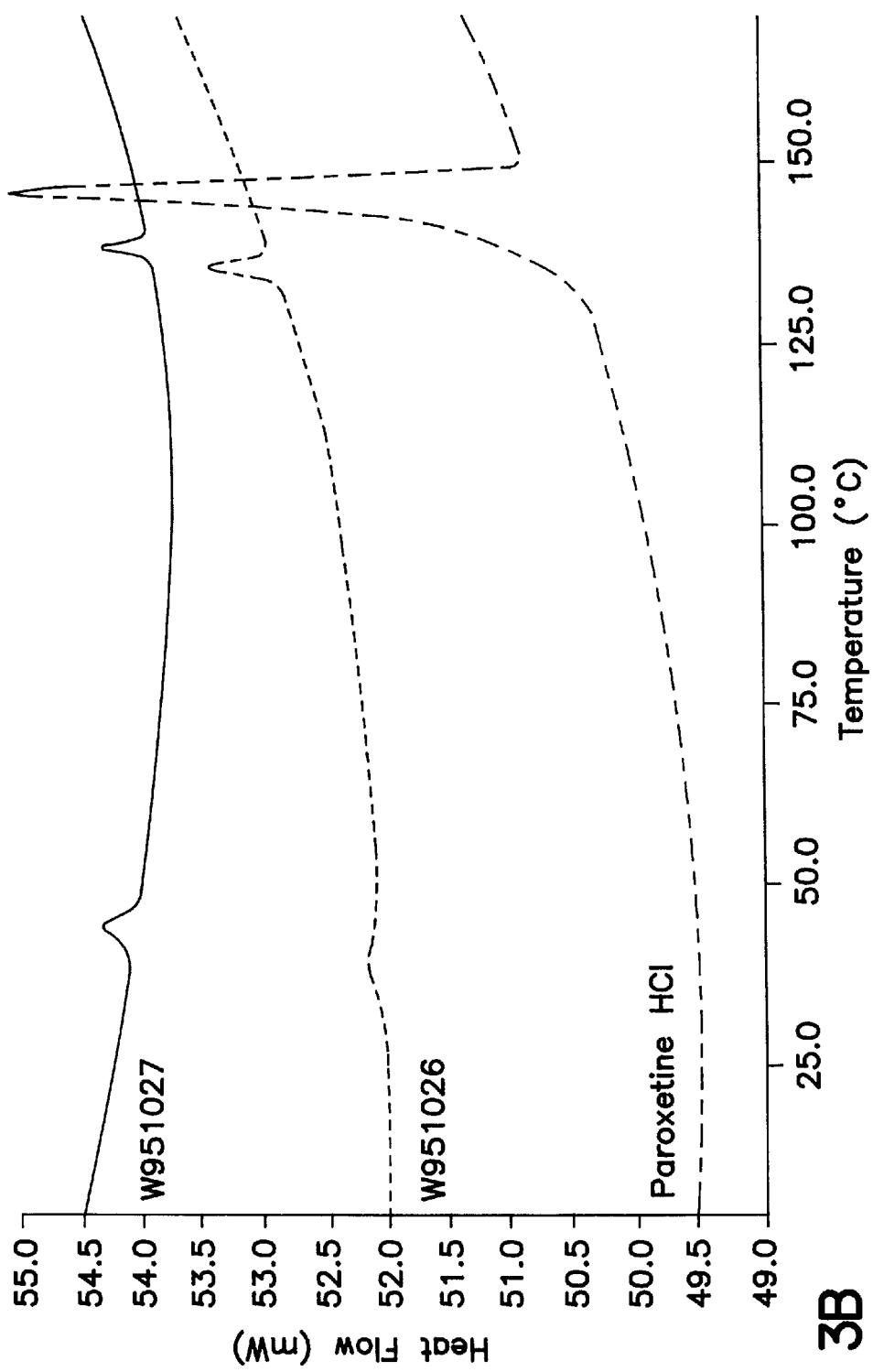
FIG. 3B illustrates the results of differential scanning calorimetry done at a heating rate of 10 degrees Celsius/minute on the reference sample paroxetine hydrochloride and two amorphous samples, lot #'s W951027 and W951026. The horizontal axis represents temperature (degrees Celsius) and the vertical axis corresponds to the heat flow (mW).

Preparation of Amorphous Paroxetine HCl-Ethanol Composition: Vacuum Drying Method To a reaction flask containing 100 ml of absolute ethanol was added 13.9 g of paroxetine base. The flask was shaken until a clear solution was obtained. To this paroxetine solution, 10 ml of a solution of hydrochloric acid in absolute ethanol (22% v/v) was added dropwise. As the reaction proceeded to completion, the color of the solution changed from a yellow brown to a pink brown. The product was then vacuum dried in a rotary evaporator. A foamy, amorphous solid was obtained (lot # W951027). The produced amorphous solid was subjected to an additional 2.5 days of drying in a desiccator at reduced pressure. The solid, a free-flowing powder, was tested for composition by NMR and FTIR. The findings were consistent with published spectra for paroxetine. Silver nitrate testing of the solid indicated the presence of chloride in the sample. Volatile analysis by gas chromatography revealed that the amount of ethanol present in the amorphous solid was 4% by weight. Residual moisture was determined by Karl-Fisher coulometric method at 0.7%. HPLC analysis revealed the material was >99% pure and essentially free from contamination. X-ray powder crystallography was conducted on the sample and produced the diffraction pattern shown in FIG. 1. X-ray powder diffraction was performed using the powder pack method. The powder patterns were obtained using a Philips PW1710 automated diffractometer, with monochromatized $CuK_\alpha$, ($K_{\alpha 1}$=1.54060 Å; $K_{\alpha 2}$=1.54438 Å) radiation. The diffractometer was equipped with a compensating slit and a graphite monochromator. It was calibrated to 0.02° (2θ) using the quartz peak at 26.660° (2θ). The minimum peak/background ratio was 0.75. This spectrum is consistent with an amorphous solid form. The halo effect is clearly seen and the intensity is small. Differential scanning calorimetry was performed on the solid at two different heating rates. The results indicate an endotherm at 48 degrees Celsius (heat flow) with and absence of other endotherms (FIG. 3A and FIG. 3B). Visual examination showed a "glassing" of the solid at this temperature.

A specimen (0.5 g) was stored in a glass container with a HDPE liner for stability testing. The container was opened and closed periodically exposing the specimen to atmospheric moisture. Moisture determination was conducted at intervals of about 3 months. Appearance of the material was noted, summarized in TABLE 1, below.

TABLE 1

| | Stability of Paroxetine-HCl/ethanol, amorphous, lot #W951027 | | |
|---|---|---|---|
| TIME | Initial | 3 months | 6 months |
| APPEARANCE | Free-flowing powder | Free-flowing powder | Free-flowing powder |
| MOISTURE | 0.7% w/w | 1.8% w/w | 2.1% w/w |

EXAMPLE 2

Figure 2:
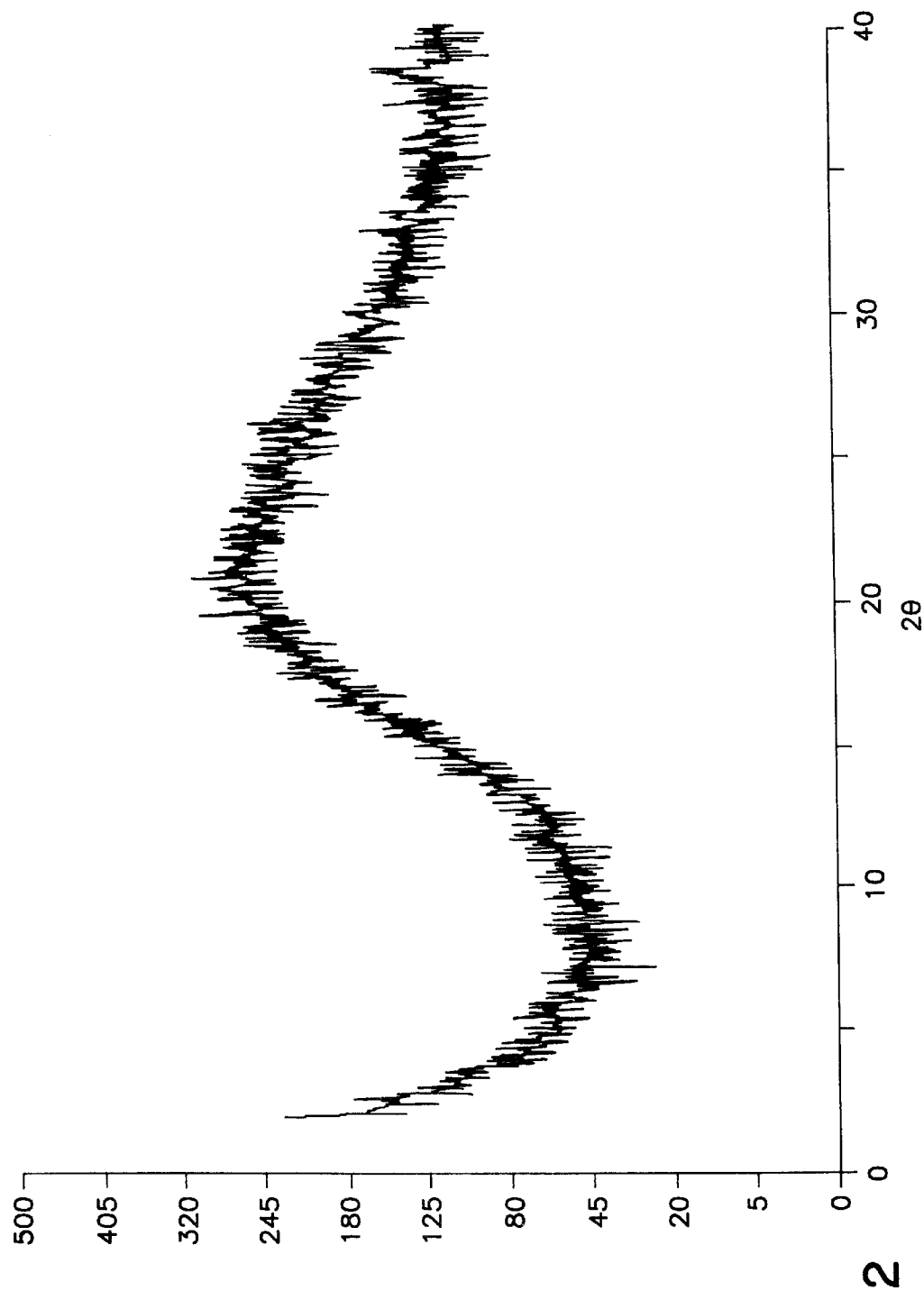
FIG. 2 is the diffraction pattern of the amorphous paroxetine composition, lot # W951026. The horizontal axis represents 2θ and the vertical axis corresponds to peak intensity.

Preparation of Amorphous Paroxetine-HCl/Ethanol Composition: Spray Drying Method A solution of paroxetine hydrochloride in absolute ethanol (3.2 g/100 ml) was prepared as described in EXAMPLE 1. The solution was charged into a spray-drying machine (Yamato Chemical Co.) using a standard nozzle (0.1 mm orifice). The inlet temperature was set at 90 degrees Celsius and the outlet temperature at 60 degrees Celsius. The sample was spray dried to a fine, off-white powder (lot # W951026). Following recovery, the material was transferred to a vacuum desiccator and dried under partial vacuum for an additional 2.5 days. The resulting solid, a free-flowing powder, was tested for composition by NMR and FTIR. The findings were consistent with published spectra for paroxetine. Silver nitrate solution addition to an aqueous solution of the powder produced a white precipitate indicative of chloride. Volatile analysis by gas chromatography revealed that the amount of ethanol residual was about 0.3% w/w. Residual moisture in the product was 0.8% measured by Karl-Fisher coulometric method. A sample was analyzed by HPLC and found to be free from related substances (purity>99%). X-ray powder crystallography was conducted producing the diffraction pattern shown in FIG. 2. This spectrum is consistent with an amorphous form. Differential scanning calorimetry was conducted on the solid. The results showed an endotherm at 48 degrees Celsius (see FIG. 3A and FIG. 3B). Visual examination of the sample showed a "glassing" of the solid at this temperature.

For stability testing a specimen (9 g) was stored in a glass container with a HDPE liner. The container was opened and closed periodically exposing the specimen to atmospheric moisture. Moisture determination was conducted at intervals of about 3 months. Appearance of the material was noted with the findings summarized in TABLE 2, below.

TABLE 2

Stability of Paroxetine HCl/ethanol, amorphous, lot #W951026

| TIME | Initial | 3 months | 6 months |
| --- | --- | --- | --- |
| APPEARANCE | Free-flowing powder | Free-flowing powder | Free-flowing powder |
| MOISTURE | 0.8% w/w | 2.1% w/w | 2.2% w/w |

EXAMPLE 3

Preparation of Amorphous Paroxetine HCl Composition Containing Citric Acid

Figure 4:
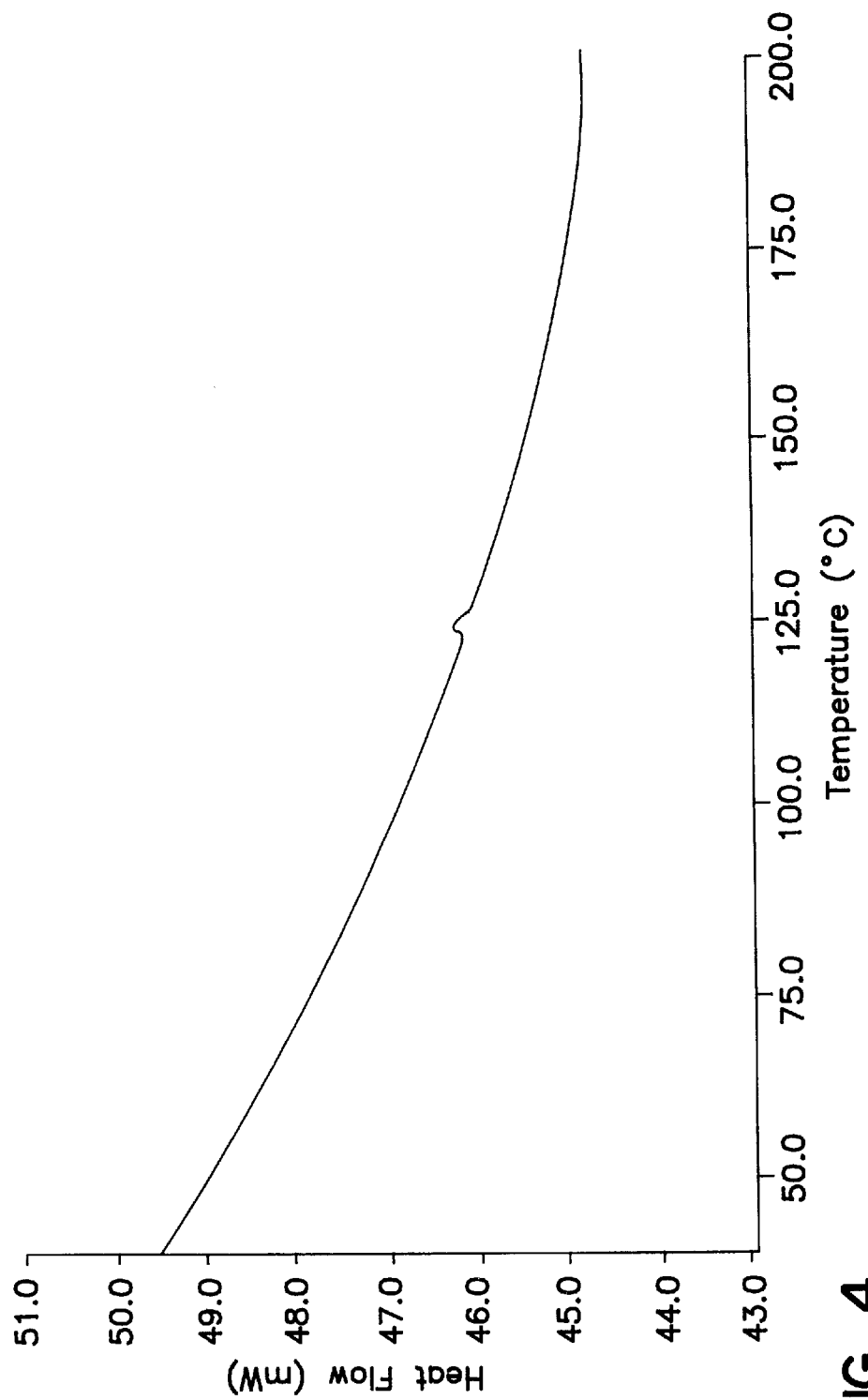
FIG. 4 illustrates the results of differential scanning calorimetry done at a heating rate of 10 degrees Celsius/minute on the amorphous paroxetine hydrochloride and citric acid composition. The horizontal axis represents temperature (degrees Celsius) and the vertical axis corresponds to the heat flow (mW).

Amorphous paroxetine HCl (3 g, prepared as described in either Example 1 or Example 2 above) was dissolved in 200 ml of absolute ethanol. Citric acid (1.0 g, citric acid anhydrous, USP) was dissolved in the ethanolic paroxetine solution. The resulting solution was clear with no detectable discoloration. The resulting solution was placed in a Büichi Model 190 mini-spray dryer with the following parameters: inlet temperature, 65–72 degrees Celsius; outlet temperature, 50–60 degrees Celsius; aspirator setting −30 millibar, air flow rate of 400 ml/minute. The resulting product is a solid amorphous paroxetine composition that is a white to off-white fine powder. The results of differential scanning calorimetry of the product are shown in FIG. 4.

EXAMPLE 4

Preparation of Amorphous Paroxetine HCl Composition Containing Polyvinyl Pyrrolidone Amorphous paroxetine HCl (5 g, prepared as described in either Example 1 or Example 2 above) was blended with 1.87 g polyvinyl pyrrolidine (Kollidon 30, BASF). To this blend was added 2.5 ml of an ethanolic citric acid solution, which was prepared by dissolving 0.25 g citric acid in 5.0 ml absolute ethanol, and blending was continued. The resulting blend was spread on the bottom of a stainless steel pan and dried for 4 hours at 65 degrees Celsius. The dried blend was milled and passed through a 30 mesh (A.S.T.M.) stainless steel screen. The final granulation size of the product was determined by the mesh size of the sieve.

Figure 5:
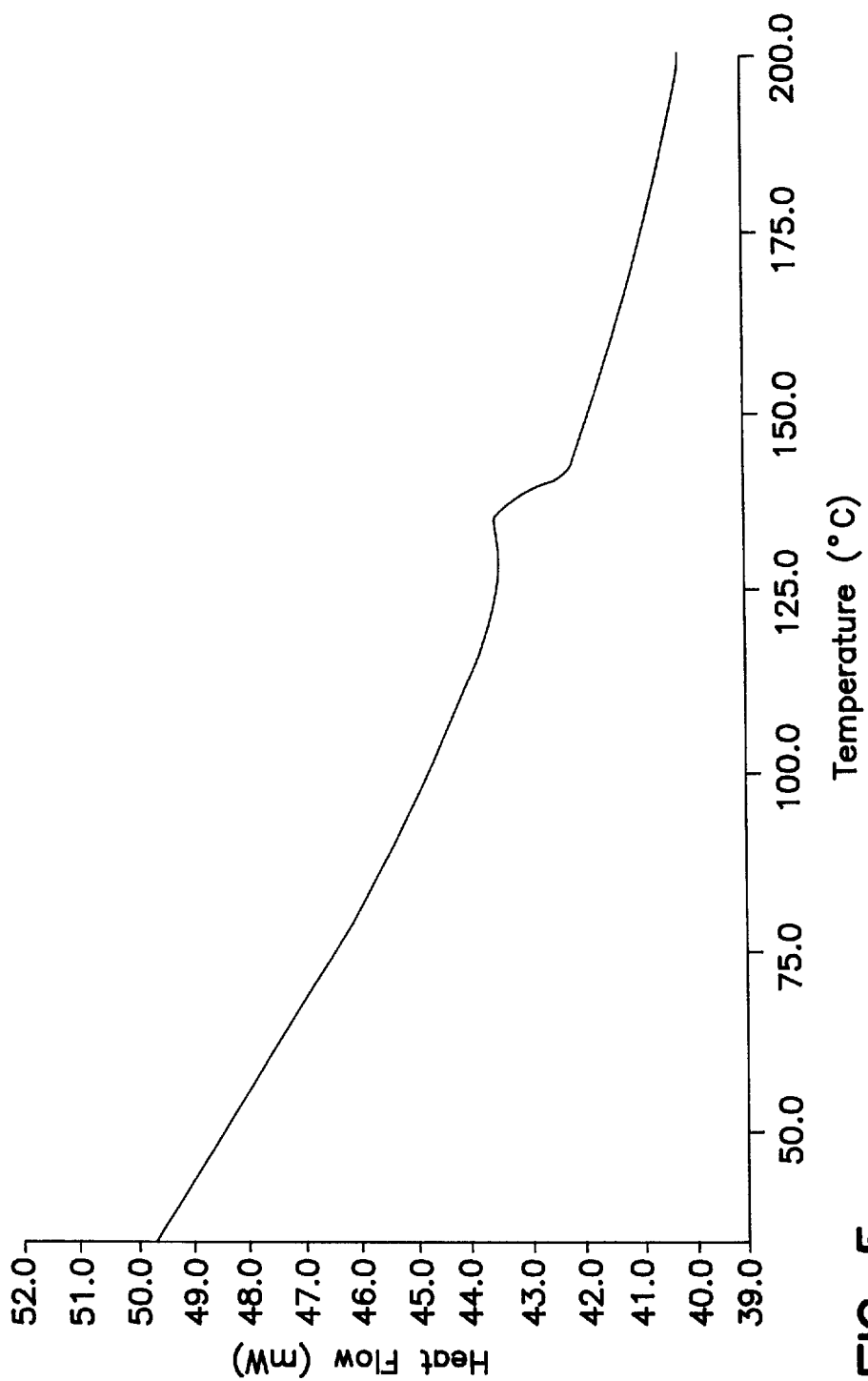
FIG. 5 illustrates the results of differential scanning calorimetry done at a heating rate of 10 degrees Celsius/minute on the amorphous paroxetine hydrochloride and polyvinyl pyrrolidine composition compressed into a tablet. The horizontal axis represents temperature (degrees Celsius) and the vertical axis corresponds to the heat flow (mW).
Figure 6:
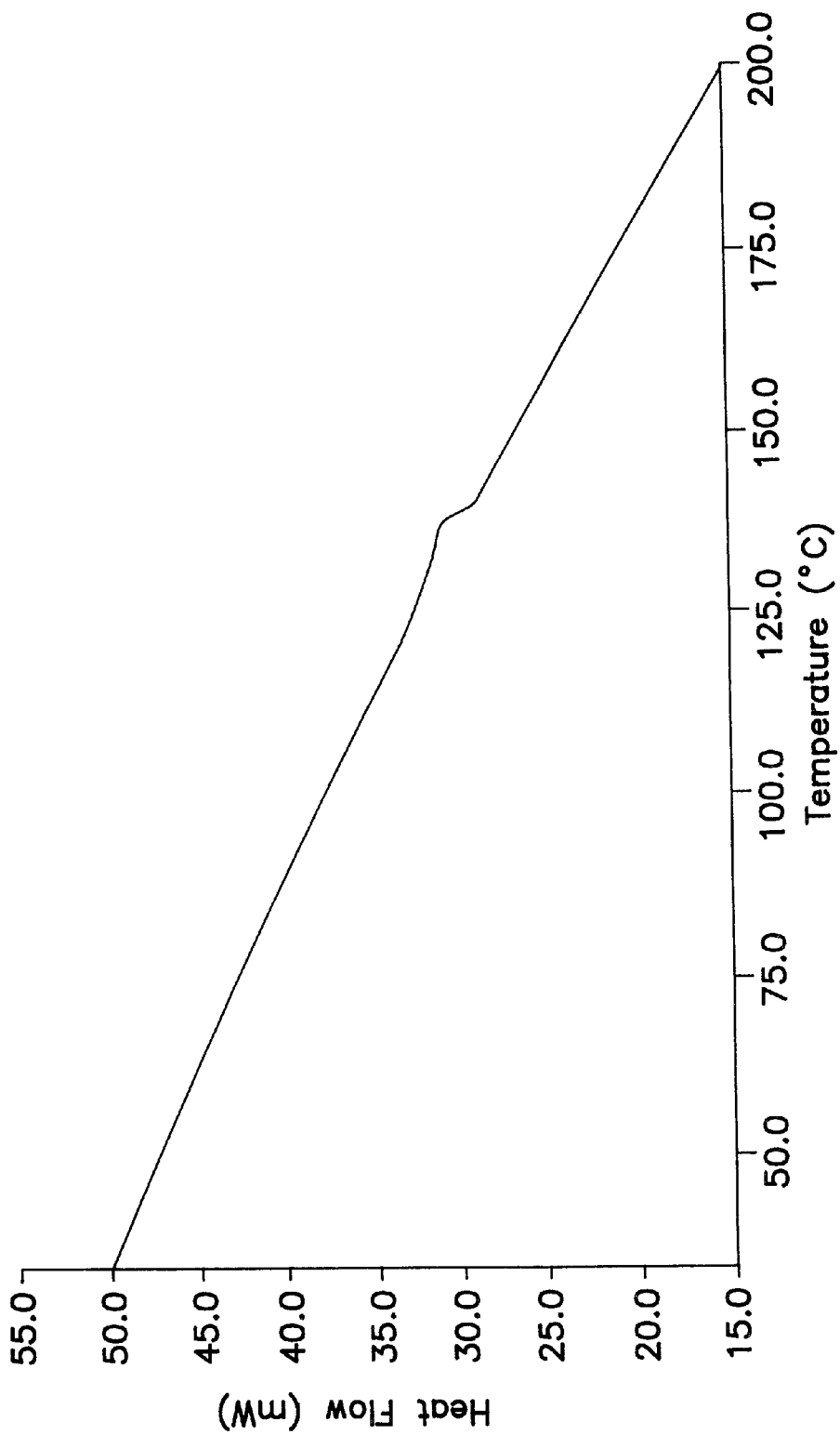
FIG. 6 illustrates the results of differential scanning calorimetry done at a heating rate of 10 degrees Celsius/minute on the granulated amorphous paroxetine hydrochloride and polyvinyl pyrrolidine composition. The horizontal axis represents temperature (degrees Celsius) and the vertical axis corresponds to the heat flow (mW).

An aliquot of final granulated product when tested for tablet compression produced an elegant tablet with a hardness of greater than 5 Kp. The results of differential scanning calorimetry of the compressed tablet are shown in FIG. 5. The results of differential scanning calorimetry of the granulated product are shown in FIG. 6.

EXAMPLE 5

Figure 7:
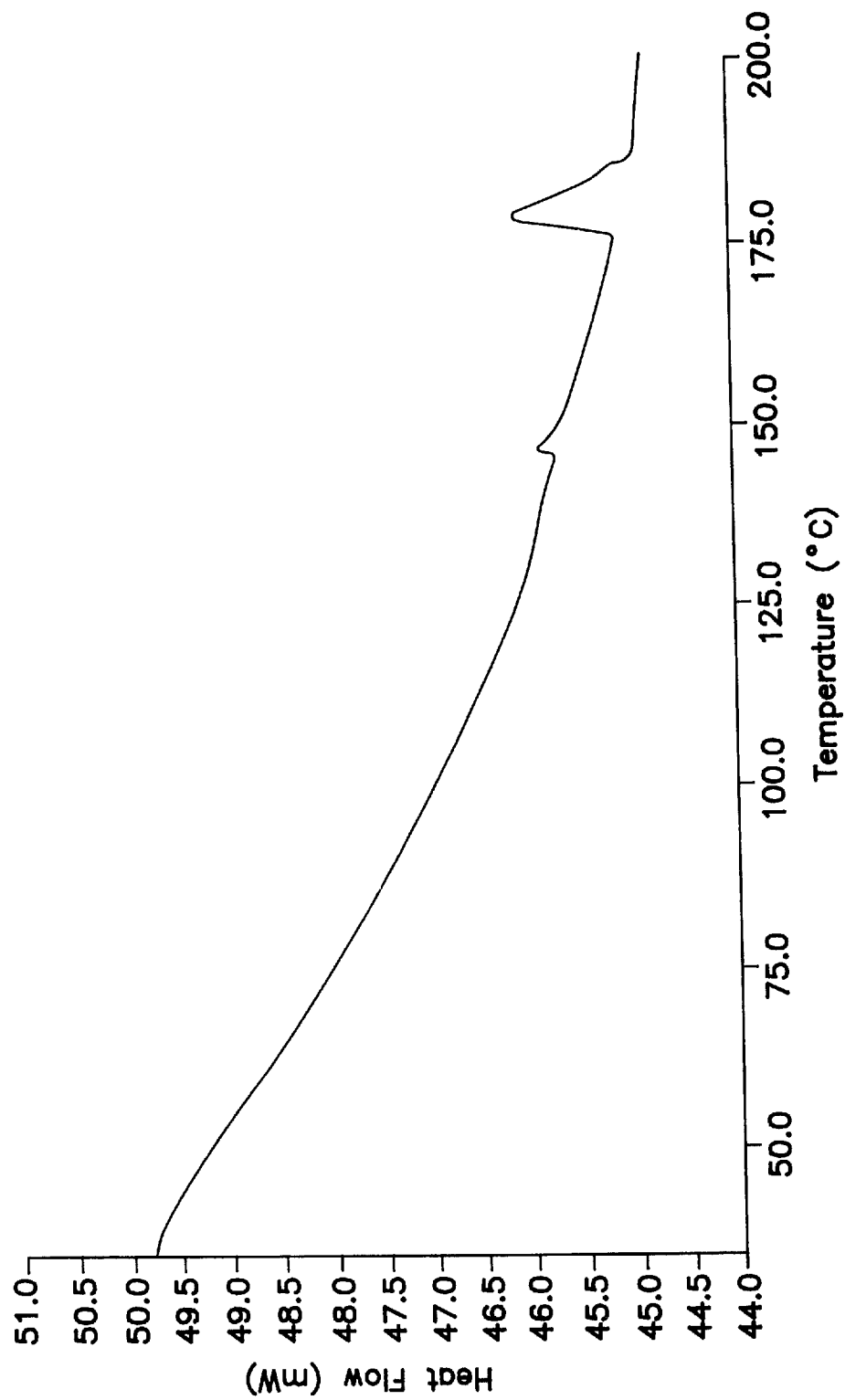
FIG. 7 illustrates the results of differential scanning calorimetry done at a heating rate of 10 degrees Celsius/minute on the free-flowing powder amorphous paroxetine hydrochloride and hydroxypropyl-beta-cyclodextrin composition. The horizontal axis represents temperature (degrees Celsius) and the vertical axis corresponds to the heat flow (mW).

Preparation of Amorphous Paroxetine HCl Composition Containing Hydroxypropyl-beta-cyclodextrin Amorphous paroxetine HCl (2 g, prepared as described in either Example 1 or Example 2 above) was dissolved in 150 ml absolute ethanol. Hydroxypropyl-beta-cyclodextrin (5 g) was dissolved in this solution, and the resulting solution was dried under vacuum to yield a free-flowing powder. The results of differential scanning calorimetry of the free-flowing powder are shown in FIG. 7.

EXAMPLE 6

Preparation of Amorphous Paroxetine HCl Solid Dispersions

Amorphous paroxetine HCl in the form of a very fine spray dried powder can have a static charge. The extremely small particle size (few micrometers in diameter) in addition to the static charge resulted in mixing uniformity problems with pharmaceutical excipients, requiring a large percentage of lubricants and anti-static agents in the capsule formulation. Solid dispersions of paroxetine were prepared as new compositions suitable for the preparation of a tablet formulation of amorphous paroxetine HCl. The objective of this study was to prepare a solid dispersion containing paroxetine, citric acid and Kollidon 30 (PVP 30). The solid dispersion is suitable for use in formulating an oral dosage form such as a tablet or capsule.

The materials used were in this composition were paroxetine HCl, amorphous, AGC, Lot #96501; Povidon 30 (PVP 30), Kollidon 30, BASF, Lot #G33055PTO; citric acid, anhydrous, ADM, Lot S308808; absolute ethanol, McCormick, Lot #290B10635; and concentrated hydrochloric acid, Fisher, Lot #967468.

A paroxetine solid dispersion was prepared by dissolving citric acid (0.3 g) and PVP 30 (3 g) in 50 ml of ethanol in a round bottom flask. Paroxetine HCl, amorphous (7.5 g) was added along with 100 ml of ethanol and was dissolved with the aid of magnetic stirring and sonication. Concentrated hydrochloric acid (0.5 ml) was added to the resulting solution to prevent discoloration. The acidified solution was clear and slightly yellow. The acidified solution was evaporated in a roto-evaporation (Rotavap) apparatus under vacuum. The flask was immersed in 40–55 degrees Celsius bath, rotated at 190 rpm. The vacuum was increased when more than 100 ml of the ethanol was evaporated. The flask was removed from the Rotavap apparatus when no visible liquid remained. The flask was placed in a 40–50 degrees Celsius oven overnight to evaporate the remaining alcohol. The dried material was ground into powder using a mortar and pestle. Two batches, labeled #1 and #2, were prepared as described above.

The resulting solid dispersion had the appearance of a free-flowing off-white, slightly yellow powder. Paroxetine base potency in the solid dispersion was determined by HPLC to be 59.27 percent and 59.31 percent in batches #1 and #2, respectively; 33.75 mg of the solid dispersion contains 20 mg paroxetine base. Unlike amorphous paroxetine HCl powder, the paroxetine solid dispersion does not possess any noticeable static charge. The density was determined to be: bulk density, 0.536 g/ml; tapped density, 0.766 g/ml.

Figure 8:
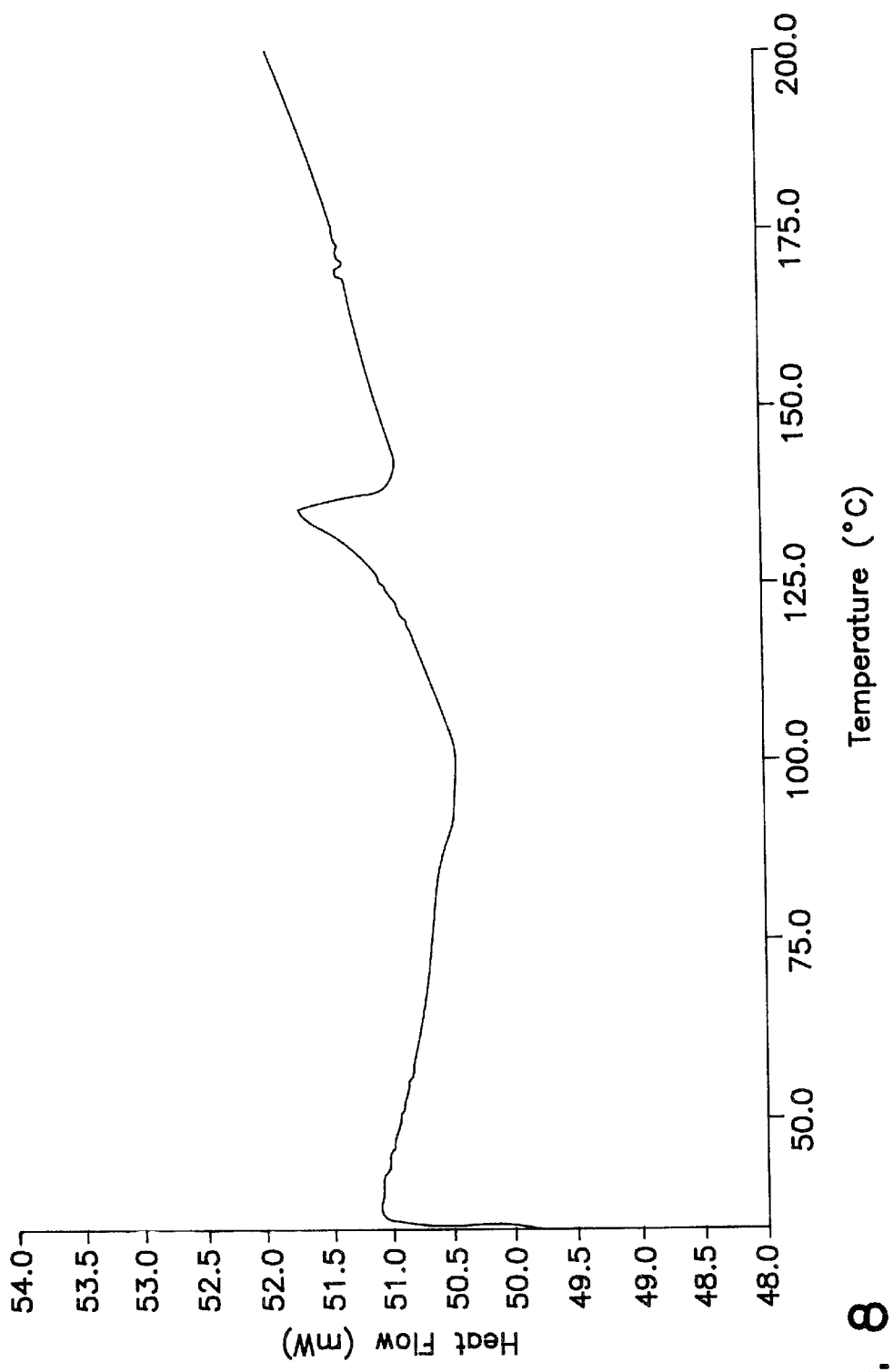
FIG. 8 illustrates the results of differential scanning calorimetry done at a heating rate of 10 degrees Celsius/minute on batch #1 of the amorphous paroxetine hydrochloride solid dispersion of Example 6. The horizontal axis represents temperature (degrees Celsius) and the vertical axis corresponds to the heat flow (mW).

Differential scanning calorimetry of batch #1 produced a thermogram (FIG. 8) that showed an endotherm that started at 99.0 degrees Celsius, ended at 140.3 degrees Celsius with a maximum peak at 135.4 degrees Celsius and an onset at 126.3 degrees Celsius. The heat of fusion was calculated to be 44.99 J/g.

Figure 9:
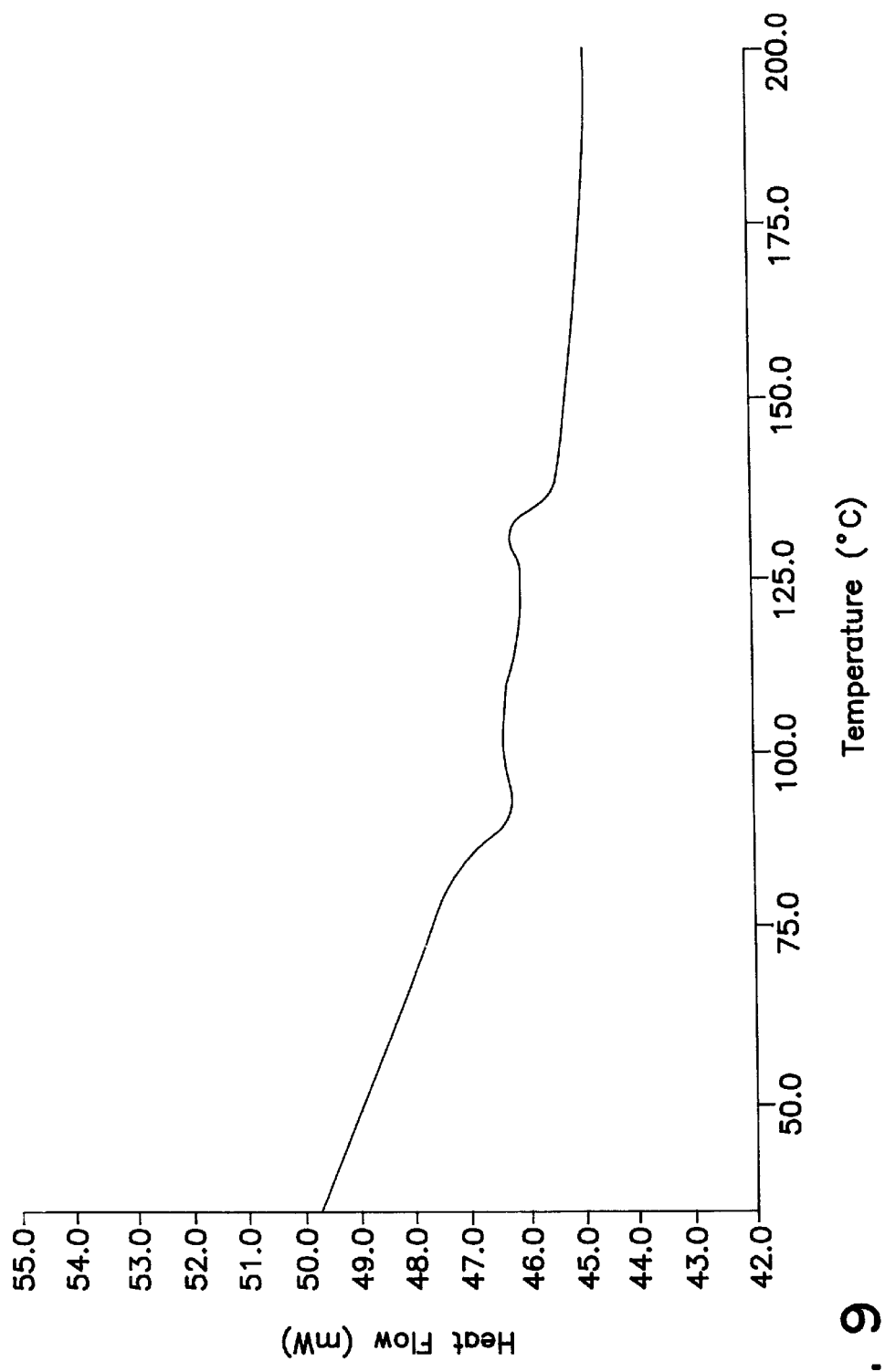
FIG. 9 illustrates the results of differential scanning calorimetry done at a heating rate of 10 degrees Celsius/minute on batch #2 of the amorphous paroxetine hydrochloride solid dispersion of Example 6. The horizontal axis represents temperature (degrees Celsius) and the vertical axis corresponds to the heat flow (mW).

The thermogram of batch #2 (FIG. 9) showed an endotherm that started at 120 degrees Celsius, and ended at 136 degrees Celsius, with a maximum peak at 131.4 degrees Celsius and an onset at 125.3 degrees Celsius. The heat of fusion was calculated to be 22.84 J/g.

EXAMPLE 7

Preparation of Additional Amorphous Paroxetine HCl Solid Dispersions

Figure 10:
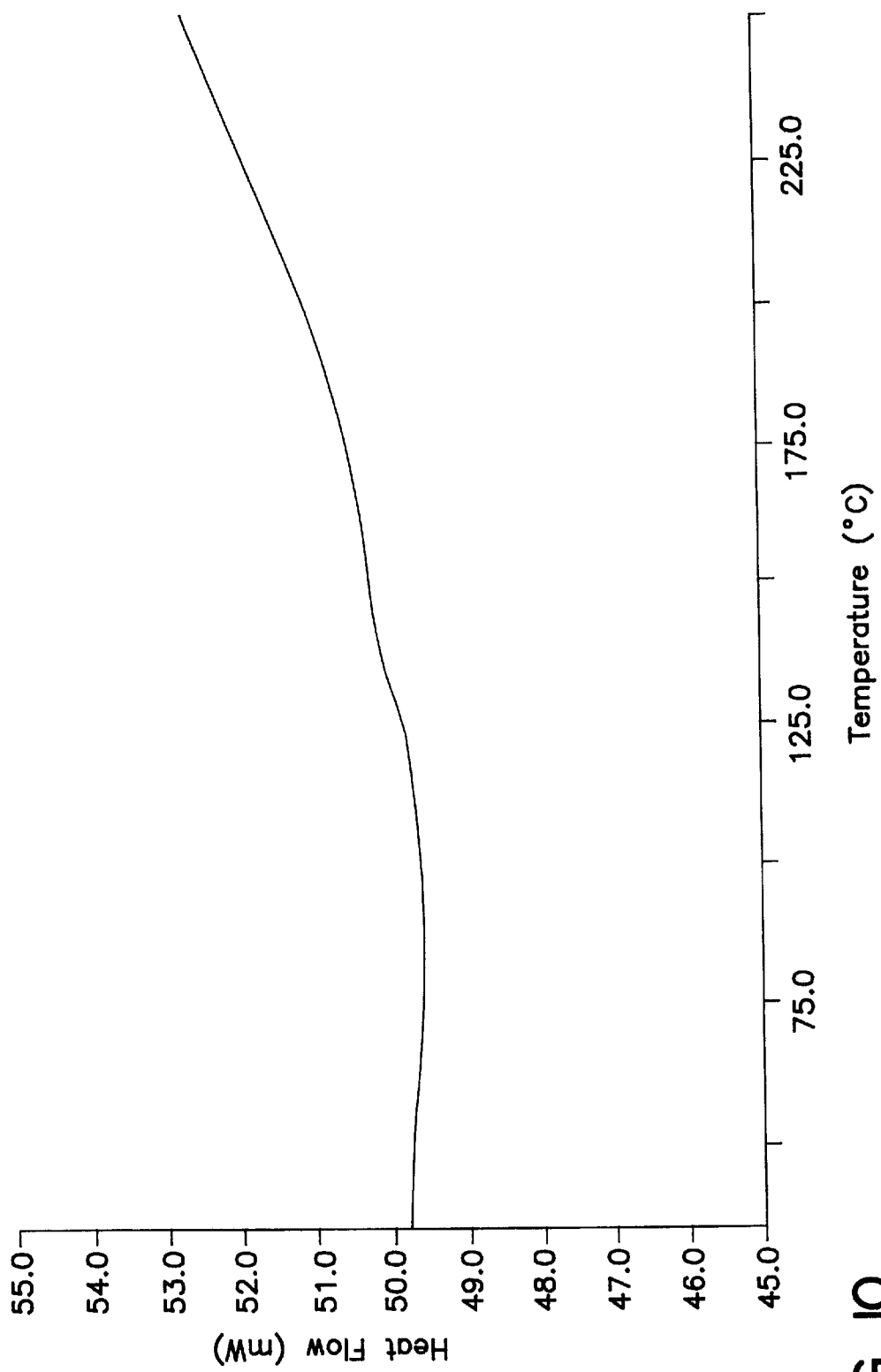
FIG. 10 illustrates the results of differential scanning calorimetry done at a heating rate of 10 degrees Celsius/minute on the amorphous paroxetine hydrochloride solid dispersion of Example 7. The horizontal axis represents temperature (degrees Celsius) and the vertical axis corresponds to the heat flow (mW).

Amorphous paroxetine HCl (1 g, prepared as described in either Example 1 or Example 2 above) was blended with 1 gram of polyvinyl pyrrolidine (Kollidon 30, BASF) and dissolved in 100 ml absolute ethanol. The resulting solution was spray dried as described in Example 2, above. The results of differential scanning calorimetry of the product are shown in FIG. 10.

Figure 11:
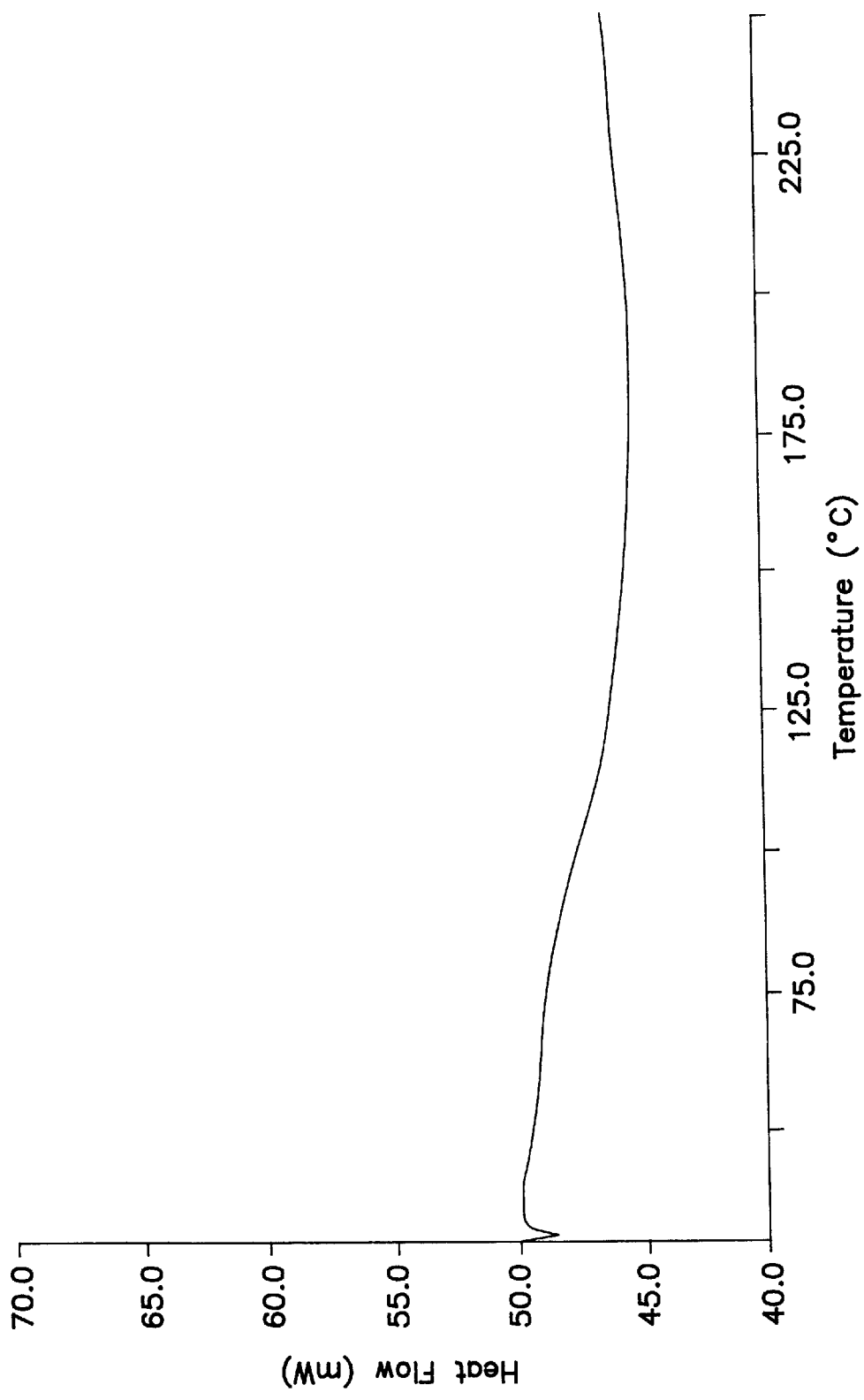
FIG. 11 illustrates the results of differential scanning calorimetry done at a heating rate of 10 degrees Celsius/minute on the amorphous paroxetine hydrochloride solid dispersion of Example 8. The horizontal axis represents temperature (degrees Celsius) and the vertical axis corresponds to the heat flow (mW).
Figure 12:
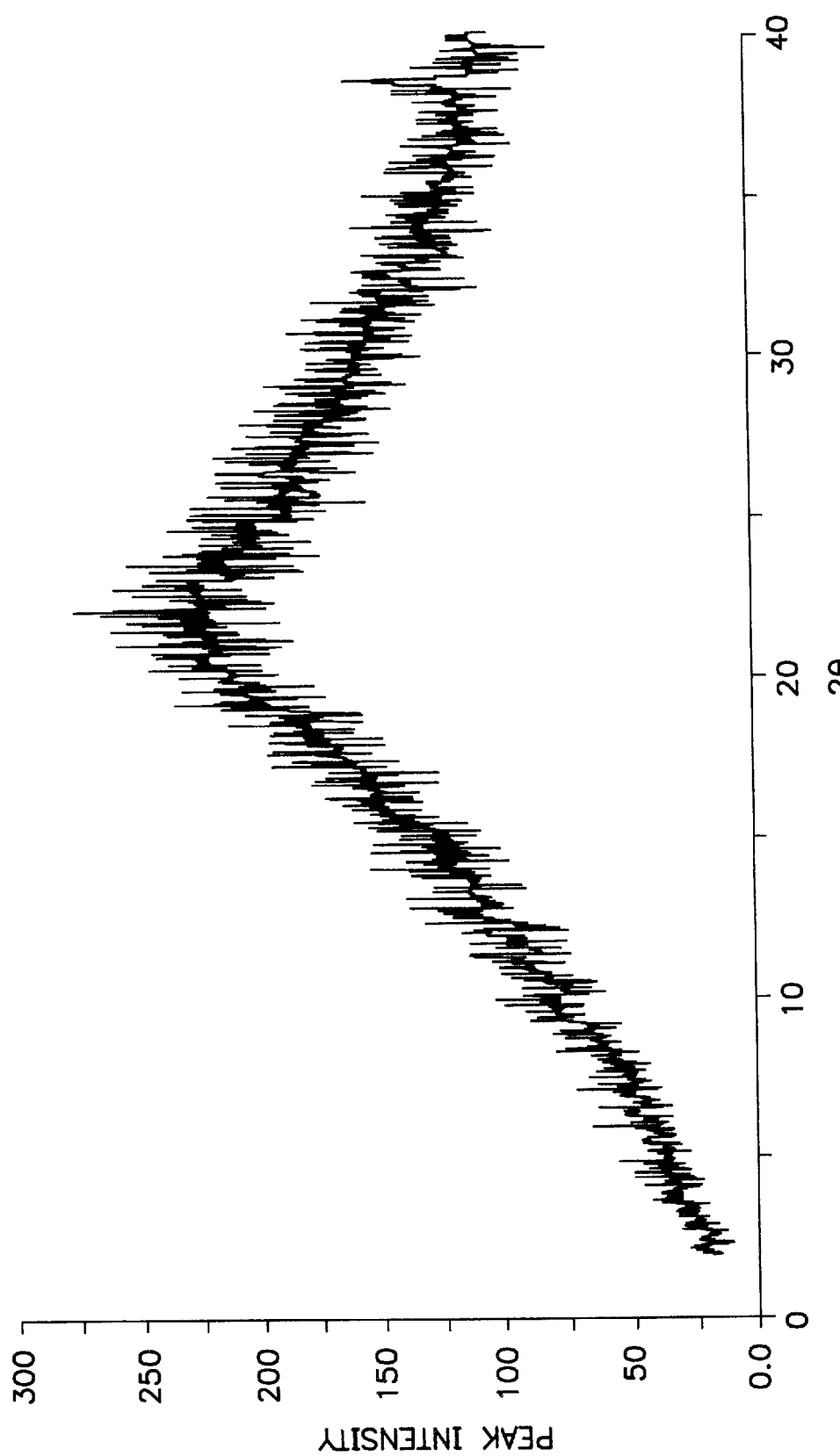
FIG. 12 is the diffraction pattern of the amorphous paroxetine composition of Example 8. The horizontal axis represents 2 θ and the vertical axis corresponds to peak intensity.

Amorphous paroxetine HCl (0.94 g, prepared as described in either Example 1 or Example 2 above) was blended with 1 g of polyvinyl pyrrolidine (Kollidon 30, BASF), 0.06 g of citric acid, anhydrous, and dissolved in 20 ml absolute ethanol. The resulting clear colorless solution was roto-evaporated under vacuum, then collected and dried further at 50 degrees Celsius overnight. The differential scanning calorimetry thermogram of the product showed no endotherms, as shown in FIG. 11. The water content of this composition determined by the Karl-Fischer method was 7.14% based on the weight of the composition. X-ray diffraction results showed the diffuse halo characteristic of amorphous paroxetine (FIG. 12).

EXAMPLE 9

Preparation of Additional Amorphous Paroxetine HCl Solid Dispersions

Figure 13:
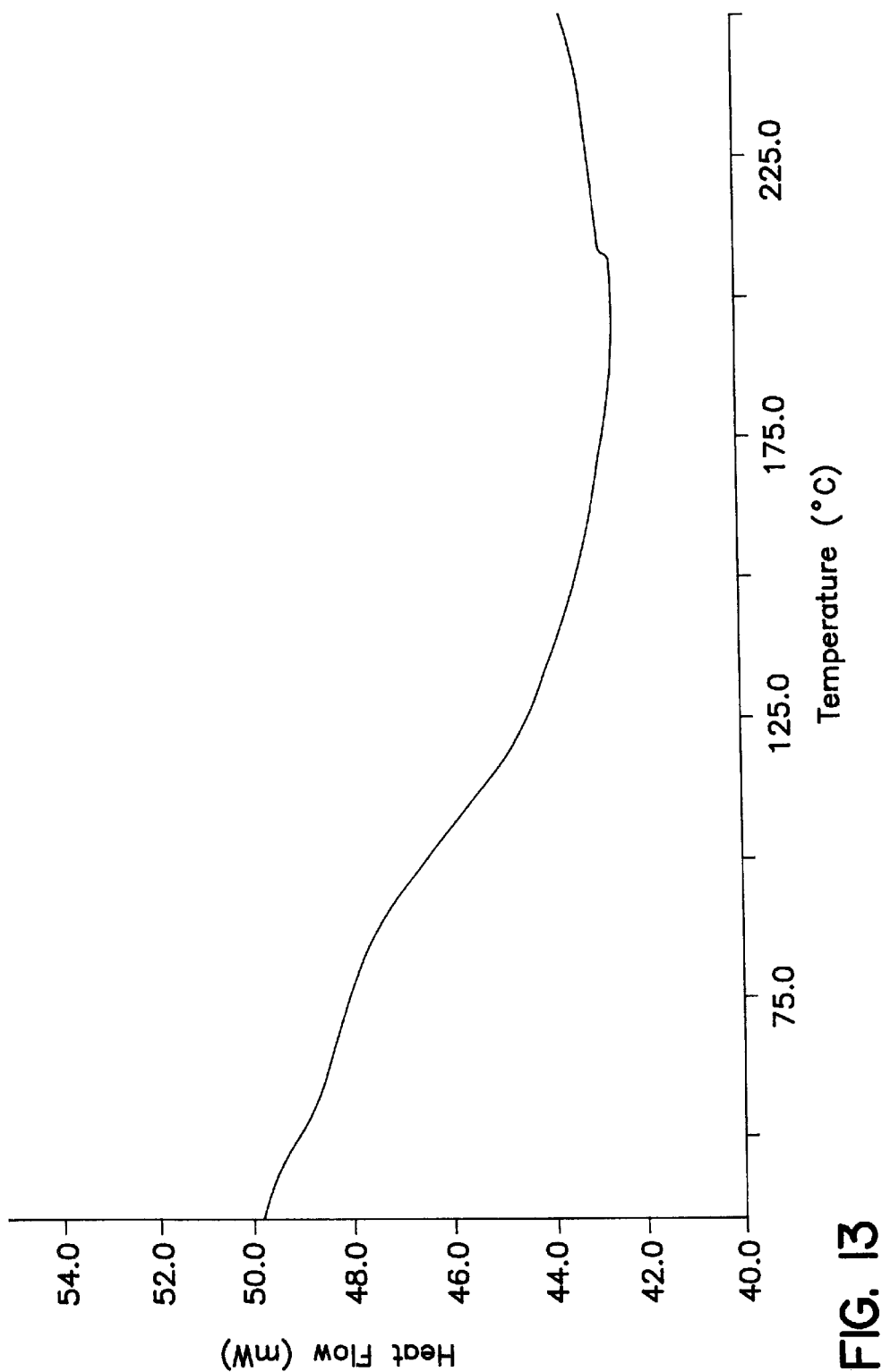
FIG. 13 illustrates the results of differential scanning calorimetry done at a heating rate of 10 degrees Celsius/minute on the amorphous paroxetine hydrochloride solid dispersion of Example 9. The horizontal axis represents temperature (degrees Celsius) and the vertical axis corresponds to the heat flow (mW).

Amorphous paroxetine HCl (0.44 g, prepared as described in either Example 1 or Example 2 above) was blended with 1.5 g of polyvinyl pyrrolidine (Kollidon 30, BASF), 0.06 g of citric acid, anhydrous, and dissolved in 20 ml absolute ethanol. The resulting clear colorless solution was evaporated under vacuum, then collected and dried further at 50 degrees Celsius overnight. The differential scanning calorimetry thermogram of the product showed no endotherms, as shown in FIG. 13.

EXAMPLE 10

Preparation of Amorphous Paroxetine HCl Capsule Compositions

Compositions suitable for capsule dosage forms were made using amorphous paroxetine HCl (prepared as described in either Example 1 or Example 2 above) and excipients. The compositions are detailed in Table 3, below.

Table 3

| 3/30 AMORPHOUS PAROXETINE CAPSULE FORMULATION Ingredient (mg/capsule) | A | B | C | D |
|---|---|---|---|---|
| Amorphous paroxetine HCl | 22.65 | 33.9 | 11.33 | — |
| Citric Acid, Anhydrous, NF | 5.34 | — | 5.34 | 5.75 |
| Microcrystalline Cellulose, NF (Avicel PH102) | 69.6 | — | 69.6 | 75.0 |
| D-Mannitol (DS 200 Perlitol) | — | 77.1 | — | — |
| Fumed Silica | 1.16 | 9.0 | 1.16 | 1.25 |
| Sodium starch glycolate | 2.32 | — | 2.32 | 2.5 |
| Dicalcium phosphate dihydrate | 130.93 | — | 142.26 | 165.5 |
| Magnesium stearate NF | — | 1.2 | — | — |
| TOTAL, mg/capsule | 232 | 121.2 | 232 | 250 |

Composition A provided a dose of amorphous paroxetine HCL equal to 20 mg amorphous paroxetine base in a 250 mg capsule. Composition B provided a dose of amorphous paroxetine HCL equal to 30 mg amorphous paroxetine base in a composition comprising D-mannitol and silicon dioxide. Composition C provided a dose of amorphous paroxetine HCL equal to 10 mg amorphous paroxetine base. Composition D is a placebo composition that contains excipients but lacks paroxetine hydrochloride.

The foregoing is intended to be illustrative of the present invention, but not limiting. Numerous variations and modifications of the present invention may be effected without departing from the true spirit and scope of the invention.

We claim:

1. A solid, stabilized amorphous paroxetine composition which comprises amorphous paroxetine hydrochloride and at least one hydroxyl-bearing compound chosen from the group consisting of a carboxylic acid, a hydroxycarboxylic acid, a sugar acid, a polyhydric alcohol, a cyclodextrin and mixtures thereof; further comprising about 20 percent to about 340 percent by weight polyvinylpyrrolidone based on the weight of amorphous paroxetine hydrochloride.

2. The composition of claim 1 wherein the hydroxycarboxylic acid is citric acid.

3. The composition of claim 1 wherein the citric acid is present in the amount of about three percent to about 25 percent by weight based on the weight of amorphous paroxetine hydrochloride.

4. The composition of claim 1 wherein the polyhydric alcohol is D-mannitol.

5. The composition of claim 1 further comprising microcrystalline cellulose.

6. The composition of claim 1 further comprising fumed silica.

7. The composition of claim 1 further comprising dicalcium phosphate dihydrate.

8. The composition of claim 1 and in capsule form.

9. A solid, stabilized amorphous paroxetine composition which comprises amorphous paroxetine hydrochloride and at least one carboxylic acid, a further comprising about 20 percent to about 340 percent by weight polyvinylpyrrolidone based on the weight of amorphous paroxetine hydrochloride.

10. A solid, stabilized amorphous paroxetine composition which comprises amorphous paroxetine hydrochloride and at least one hydroxycarbocylic acid, further comprising about 20 to about 340 weight percent by weight polyvinylpyrrolidone based on the weight of amorphous paroxetine hydrochloride.

11. The composition of claim 10 wherein the hydroxycarboxylic acid is citric acid.

12. The composition of claim 11 wherein citric acid is present in the amount of about three percent to about 25 percent by weight based on the weight of amorphous paroxetine hydrochloride.

13. A solid, stabilized amorphous paroxetine composition which comprises amorphous paroxetine hydrochloride and D-mannitol.

14. A solid, stabilized amorphous paroxetine composition which comprises amorphous paroxetine hydrochloride and at least one cyclodextrin.

15. The composition of claim 14 wherein the cyclodextrin is hydroxypropyl-beta-cyclodextrin.

* * * * *

UNITED STATES PATENT AND TRADEMARK OFFICE
CERTIFICATE OF CORRECTION

PATENT NO. : 6,638,948 B1  Page 1 of 1
DATED : October 28, 2003
INVENTOR(S) : Bruce Ronsen et al.

It is certified that error appears in the above-identified patent and that said Letters Patent is hereby corrected as shown below:

Column 1,
Line 46, "trans4R" should be -- trans-4*R* --.

Column 5,
Line 61, after "$CuK_\alpha$," delete the comma ",".
Line 65, "26.66θ°" should be -- 26.66° --.

Column 10,
Line 24, "claim 1" should be -- claim 2 --.

Signed and Sealed this

Twelfth Day of October, 2004

JON W. DUDAS
*Director of the United States Patent and Trademark Office*